United States Patent [19]

Chu

[11] Patent Number: 4,636,197
[45] Date of Patent: Jan. 13, 1987

[54] INTRAVENOUS FLUID INFUSION DEVICE

[76] Inventor: Ping Chu, 2227 Foreland, Houston, Tex. 77077

[21] Appl. No.: 702,220

[22] Filed: Feb. 15, 1985

[51] Int. Cl.$^4$ ............................................. A61M 37/00
[52] U.S. Cl. .................................... 604/131; 604/207; 128/DIG. 12
[58] Field of Search ............... 604/131, 132, 133, 184, 604/185, 186, 207, 208, 134, 135; 128/DIG. 12

[56] References Cited

U.S. PATENT DOCUMENTS

| | | | |
|---|---|---|---|
| 3,647,117 | 3/1972 | Hargest | 604/131 |
| 3,670,926 | 6/1972 | Hill | 604/131 |
| 3,884,228 | 5/1975 | Hahn | 604/131 |
| 3,895,631 | 7/1975 | Buckles et al. | 604/132 |
| 4,278,089 | 7/1981 | Huck et al. | 604/134 |
| 4,381,006 | 4/1983 | Genese | 604/135 |

Primary Examiner—John D. Yasko
Attorney, Agent, or Firm—Robert M. Carwell

[57] ABSTRACT

An infuser for dispensing medicaments to a patient at a preselected controlled flow rate. A housing unit is provided having a precalibrated flow control valve assembly portion sized to the desired flow rate. At the outer proximal end of the housing an outlet tubing or catheter is interconnected to the flow control valve assembly. A conventional syringe has its proximal end removably and sealably contained within the housing with its tip portion in sealingly mating engagement with the flow control valve assembly whereby the housing, syringe, and valve assembly are disposed in coaxial alignment. Elastomeric members are disposed on either side of the syringe and housing, each such member being anchored at opposed ends to the proximal end of the housing and the distal end of the syringe plunger. Restorative force applied to the syringe by the energy stored in the distended elastomeric members controls, over time, the force at which the plunger is introduced into the syringe housing, thereby controlling the infusion rate of the medicaments stored in the syringe.

20 Claims, 5 Drawing Figures

U.S. Patent   Jan. 13, 1987   Sheet 1 of 2   4,636,197
FIG.1
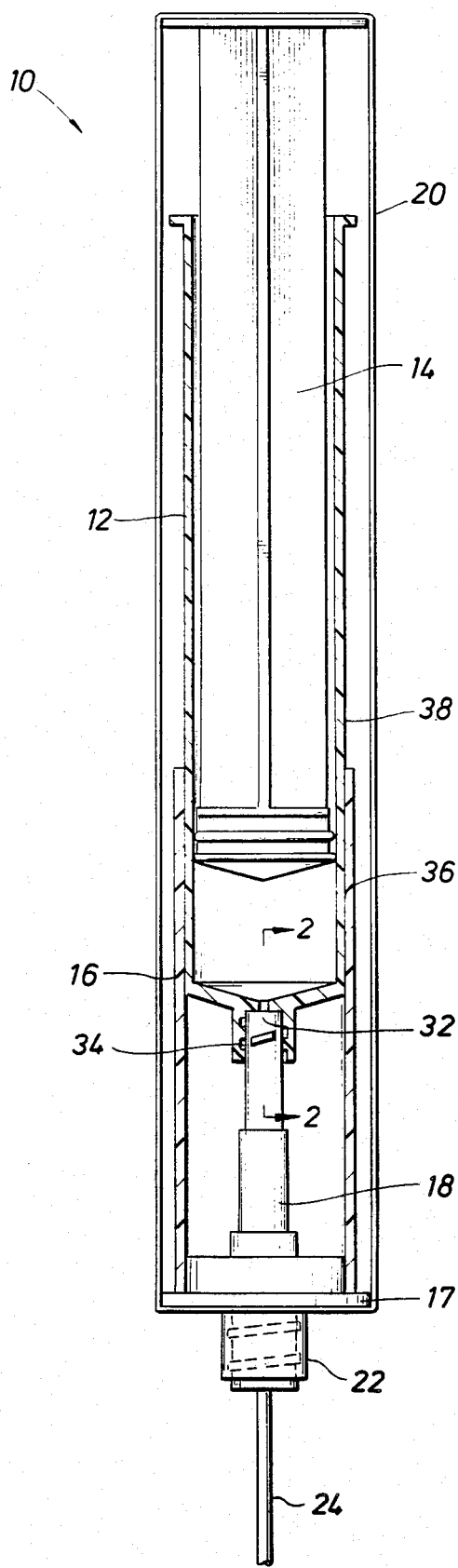
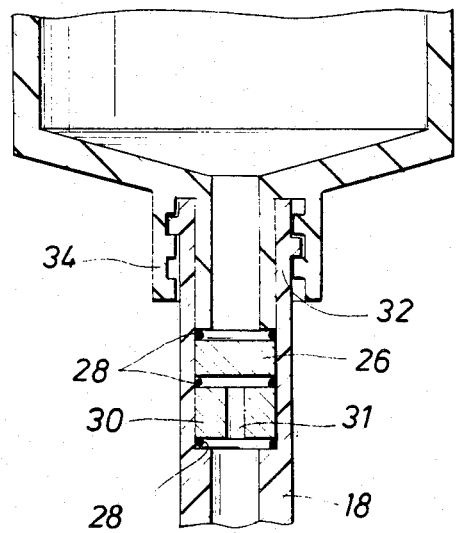
FIG. 2

INTRAVENOUS FLUID INFUSION DEVICE

BACKGROUND OF THE INVENTION

Various apparatus have long been employed for intravenous infusion of fluids into a patient at a controlled rate and over extended periods of time, the most common of these being simply a gravity flow technique wherein a container of the desired medicament, drug, or the like is suspended above the patient and infusion is effected by gravity flow of the fluid from a container suspended above the patient through a tube and into the patient. However, rather than relying simply on gravity flow, various apparatus and techniques were devised for better controlling the rate of infusion as, for example, depicted in U.S. Pat. No. 4,132,231 to Puccio and U.S. Pat. No. 4,381,006 to Genese. Such devices relied upon a system of weights or coil springs employed to activate the plunger of a conventional syringe in a controlled manner as a function of the weight or spring tension.

Such approaches suffered from serious drawbacks, not the least of which was the lack of portability, simplicity, and low cost of such devices which has become more important recently with the advent of increased frequency in ambulatory patient care. Accordingly, yet additional devices were developed to meet this need such as a spring-loaded cylindrical carrier of a conventional syringe depicted in U.S. Pat. No. 3,880,163 to Ritterscamp and like devices. Such devices still suffered from obvious drawbacks relating to the number of moving parts required, undue weight and bulk, unreliability and inflexibility of infusion rates due to difficulty in controlling and varying spring tension over time and related mechanical complexity problems, and the like, giving rise to the need for a simpler drug dispensing device. Recently, such a device has been developed as depicted in U.S. Pat. No. 4,201,207 to Buckles, et al. In such apparatus, an elastomeric reservoir in the form of a bladder is provided which is distended upon filling of the bladder with the drug to be administered. In some forms, the bladder apparatus is provided in the form of a cylindrical balloon disposed within a rigid housing. The energy stored in the resilient walls of the distended elastomer provides the force required to infuse the drug contained within the bladder through an appropriate tube and into the patient.

Unfortunately, while solving at least the problem of portability, such devices have suffered from numerous other drawbacks. First, there have been problems in such continuous infusion devices with establishing a constancy of delivery rate of the drug thought to be caused by a loss of pressure provided by the bladder for a constant volume with time. Moreover, it has been found that excessive retention of drugs within the bladder occurs after a complete retraction of the elastomer, i.e., it is difficult to completely evacuate the bladder during the infusion process. This in turn has been found extremely undesirable inasmuch as some of the drugs which are administered are extremely expensive and it has been found that loss rates by volume ranging from 5–25% of the drug have been experienced. It has oftentimes also been found difficult to prime such apparatus and to manually control the infusion rate if desired. Problems have also been experienced with the bladder breaking or leaking which can at times be extremely serious not only due to the wastage of drugs and dangerous conditions which may arise if the required dosage is not thus administered, but additionally due to the deleterious effect of some of the drugs when they are contacted by those for whom they are not intended. For example, it has long been known that cancer treatment drugs are themselves carcinogenic to various degrees and it is thus highly undesirable for hospital pharmacists, nurses and other personnel administering the drugs to come into contact with them on a frequent and recurring basis. However, the possibilities of this happening have been found to be undesirably great with respect to bladder-type infusion devices due to the aforementioned breakage, leakage, and the like.

Still other problems are also associated with the bladder-type infusion devices as well as other types of devices employing, for example, motors and batteries to effect the pumping of the drug through the tube. Many of these devices are difficult to adjust in terms of flow rate, particularly with respect to the bladder-type devices. Regarding the electronic devices employing motors, instrumentation, and the like, they obviously suffer from the drawback of being more complicated, costly, requiring recharging of batteries if in a portable version, as well as difficulty in instructing the patient in proper use. Whereas the bladder-type devices are certainly more disposable than other apparatus for infusing drugs, difficulty has further been experienced in sporadic flow rates thought to be caused by varying pressures exerted by the bladder on the drug, such pressures being dependent upon the volume of the drug contained within the bladder reservoir and also being temperature dependent.

Thus, a portable continuous infusion device was highly desired which would be both of a simple construction, easy to use, portable, concealable, and of a low cost so as to render it partially disposable while at the same time providing portions which are re-usable. Moreover, such a device was further highly sought after which required no maintenance, provided for a completely sealed drug in the event of syringe tip breaks and cracks and the like so as to avoid contamination, mess, and the aforementioned problems associated with medical personnel coming in contact with the drugs. Such an infusion device was also sought which employed a conventional syringe for ease of charging the device with the desired drug inasmuch as pharmacists, nurses, and the like may in a typical day have to prepare as many as 50 or 60 such devices for use by patients. Still further, improvements were sought in the ability of the device to be easily adjusted in terms of flow rate so as to contribute to a more predictable flow rate. It was further desired to avoid the aforementioned problems associated with wastage of the drug due to the bladder's inability to entirely evacuate the drug. These and other deficiencies of the prior infusion devices are overcome by the present invention and a novel portable continuous infusion device is provided achieving all of the hereinbefore noted and sought after characteristics as well as other.

SUMMARY OF THE INVENTION

An infuser for dispensing medicaments to a patient at a preselected controlled flow rate. A housing unit is provided having a precalibrated flow control valve assembly portion disposed therein and sized to permit a preselected desired flow rate therethrough. At the outer proximal end of the housing an outlet tubing or catheter is interconnected to the flow control valve assembly. A conventional syringe has its proximal end removably and sealably contained within the housing with its tip portion in sealingly mating engagement with the flow control valve assembly whereby the housing, syringe, and valve assembly are disposed in coaxial alignment. Elastomeric members are disposed on either side of the syringe and housing, each such member being anchored at opposed ends to the proximal end of the housing and the distal end of the syringe plunger. The members have resiliency characteristics over time when distended which vary in a preselected functional fashion to provide a force against the plunger which varies in a preselected magnitude function over time. Restorative force applied to the syringe by the energy stored in the distended elastomeric members controls, over time, the force with which the plunger is introduced into the syringe housing. The infusion rate through the tube of the medicaments stored in the syringe is thereby controlled over time by the functional relation between the flow characteristics through the control valve and the resiliency characteristics of the elastomeric member.

In accordance with the method of the present invention, a filler needle is attached to a syringe which may be of conventional design. The syringe is charged with the desired drug to be infused in a conventional manner, whereupon the needle is removed.

A flow control valve having the desired preselected flow characteristics is thence disposed within the control unit contained within the housing unit of the present invention. The syringe is thence inserted partially within the housing unit and fluid interconnection established therebetween. The elastomeric member is thence interconnected between the housing unit and the syringe plunger, said member being preselected in functional relation to a preselected flow rate over time of the fluid through the tube. Fluid communication from the housing unit to the patient is thence established by means of tubing connected at one end to the housing unit and at the other intraveneously to the patient.

BRIEF DESCRIPTION OF THE DRAWINGS

FIG. 1 is a side view, partially in section, depicting an embodiment of the present invention.

FIG. 2 is an enlarged view of a portion of the invention depicted in FIG. 1.

DETAILED DESCRIPTION OF THE INVENTION

Figure 3:
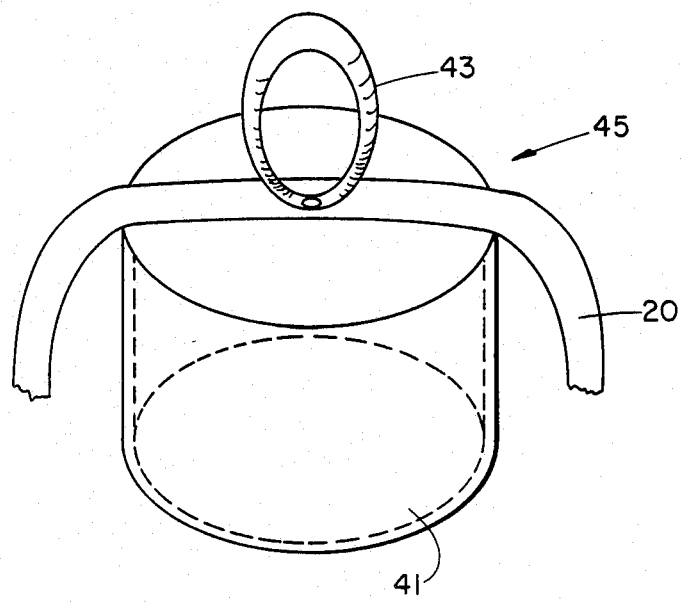
FIG. 3 is a pictorial view of a cap for use with the apparatus depicted in FIG. 1.

Referring to FIG. 1, there will be seen depicted therein generally an infuser 10 of the present invention. The infuser 10 will be seen to be comprised in general of a conventional syringe disposed in part in a generally cylindrical housing and an outlet tubing interconnected to the syringe by means of a control unit, and finally a resilient member for forcing the syringe plunger into the syringe housing in a controlled manner, all such components of the infuser 10 to be hereinafter described in greater detail. For convenience, it will be noted that, with respect to a particular component, the end thereof appearing in a figure in the upwardmost location will be referred to as the proximal end, and conversely, the end of the component appearing in a figure in a generally downward direction relative to the proximal end will be referred to as the distal end of the component.

Still referring to FIG. 1 but in greater detail now, the infuser 10 will be seen to include a syringe housing or barrel 12 which carries disposed at least partially therewithin a syringe plunger 14, the proximal end of the barrel 12 including a female luer lock adaptor 34. Thus, the barrel 12 and plunger 14 will preferably comprise a conventional syringe assembly, absent the needle of course, which is well known and conventional in the medical arts.

Still referring to FIG. 1, the proximal end of the barrel 12 will be seen to be disposed partially within a cylindrical housing unit 16 which is preferably fashioned of a transparent and rigid or semi-rigid plastic. An O-ring 11 is carried by housing 16 for fluid sealing between housing 16 and syringe housing 12. The housing is sealedly capped at its proximal end by means of a plug 17. Preferably, disposed on the proximal side of the plug 17 is another luer lock adapter 22 which receives a kink-resistant outlet tubing 24. On the distal side of plug 17 is further disposed a control unit 18 in fluid communication through plug 17 with adapter 22 and tubing 24 and terminating in a male luer lock adapter 32. A shoulder 13 in the form of a ring or four extensions in quadrature extending radially inward from housing unit 16 mate against and support barrel 12 to take weight of barrel 12 off adapter 32.

The distal end of control unit 18 is further in matingly releasable engagement with the aforementioned proximal end of barrel 12 by means of interconnection of luer lock adapters 32 and 34. The opposing end of the tubing 24 will, of course, be routed to an appropriate needle catheter or other conventional delivery device for insertion into the patient whereby fluids contained within the syringe will be delivered through the control unit 18, through the adapter 22 and tubing 24 and into the patient in a manner to be hereinafter described.

A hydrophobic venting aperture 15 preferably extends through plug 17 whereby air may pass therethrough but not liquids. This eases insertion of barrel 12 into housing unit 16 whereby air in unit 16 may evacuate through aperture 15 during insertion of barrel 12 into unit 16 without permitting fluid leakage through aperture 15. As described previously, the proximal end of the barrel 12 is provided with a female luer lock adapter 34 which is designed to sealingly and matingly engage the corresponding male luer lock adapter 32 which comprises the distal portion of the control unit 18. Thus, in assembly, the barrel 12 and plunger 14 will first be disposed adjacent a reservoir containing the drug to be administered, with a conventional needle being inserted into the female adapter 34. The needle (not shown) will be inserted into the reservoir and the plunger 14 withdrawn from the housing 12, whereupon the drug to be administered will be drawn into the cavity 13 defined by the barrel 12 and the proximal tip-end of the syringe plunger 14. Upon filling the cavity 13 to the desired amount, as indicated for example, by gradations 38 provided by a label or the like on the outer surface of the housing 12, the needle will be withdrawn from the drug reservoir and removed from the barrel 12. The barrel-plunger combination 12-14 will thence be aligned with the housing unit 16 coaxially whereupon the male and female lock adapters 32 and 34, respectively, will be disposed in mating sealable engagement by means of a twisting motion. In assembly, the infuser 10 upon thus being charged, will be as depicted in FIG. 1 with the barrel 12, plunger 14, housing unit 16, and control unit 18 coaxially aligned along a common longitudinal axis. It will be noted that in the embodiment depicted in FIG. 1, a luer-type connection is provided by the adapters 32 and 34, whereby such male and female mating connectors may be sealably and releasably joined by the corresponding mating threads in a twisting motion as is well known in the art. However, it will be readily apparent that any such fluid-type sealing connector known in the art may be substituted therefore.

An elastomeric member 20 will further be provided extending from the housing unit 16 adjacent plug 17 along either side of housing unit 16, barrel 12 and plunger 14, and terminating at the distal end of plunger 14.

With reference now to FIG. 2, a more detailed view of the proximal end portion of the barrel 12 and the distal end portion of the control unit 18 will be seen. Disposed within the control unit 18 is preferably a microporous filter 26 which may, in a typical application, have a nominal interstitial porosity of 5.0 microns. In coaxial alignment with the filter 26, sealing O-rings 28 may be provided and an adjustable precalibrated capillary 30. The capillary 30 will include an orifice 31 which is preselected in a manner well known in the art so as to control the rate of flow of drug from the chamber 13 through the orifice 31, and thus through the tubing 24. It will be readily appreciated that the sizing of this capillary 30 is critical to achieving the desired flow rate, as is the elastic characteristics of the elastomeric member 20, the parameters controlling flow through the capillary 30 and restoring force provided by the elastomeric member 20 being preselected in functional relation to achieve this desired flow rate. With respect to the capillary 30, for example, it is well known that such constrictors obey the well known Poiseuille's Law wherein $$V = \frac{\pi R^4 \Delta P}{8LN}$$

where
V = flow rate
R = the capillary radius of the orifice 31
L = the length of the orifice 31 in the longitudinal direction
$\Delta P$ = the pressure differential at the two ends of the orifice 31
N = the viscosity of the fluid flowing through the orifice 31.

From the foregoing, it will be appreciated that the capillary 30 may be designed in a conventional manner to deliver a flow rate of drugs at the desired rate. Moreover, by simply changing out the capillary 30 for one having differing parameters, the flow rate can be changed at will very simply and conveniently.

With reference to the elastomeric member 20, as aforementioned, the restoring force of this member being imparted on plunger 14 in conjunction with the previously described parameters effecting flow rate through the capillary or orifice 31 of the capillary 30, will dictate the ultimate flow rate of the drug being infused into the patient through the tubing 24. Thus, it is fully contemplated as being within the scope and teachings of the present invention to preselect the elastomeric member 20 so as to provide any desired variation in restoring force over time being imparted on the plunger 14 by varying the composition and dimensions of the elastomeric member 20. Thus, for example, by appropriate selection of these parameters of the elastomeric member 20, the restoring force and thus the infusion rate may be preselected to be linear over time or any non-linear function of time as desired. It has been found that a desirable construction of the elastomer 20 is to fashion it of an poly-isoprene rubber, natural rubber, or an isobutylene/isoprene rubber. Further details of the composition and design of the elastomer 20 may be found with reference to a publication entitled "Role of the Elasticity of Rubber in the Controlled Administration of Drugs" by H. M. Leeper, et al, *Rubber Chemistry and Technology*, Vol. 50, No. 5, November-December 1977, which is hereby incorporated for all purposes by reference.

Also with reference to the member 20, in the embodiment depicted one member extending in opposed relation on either side of housings 12 and 16 have been shown. However, it is fully contemplated by the present invention and should be apparent that it may be preferable to provide in some applications a member 20 in the form of only one length, or alternatively three or more lengths of resilient material disposed circumferentially about housings 12 and 16 and extending from housing 16 to plunger 14.

Referring to FIG. 3, there is depicted therein a pictorial view of a cap 45 for use with the apparatus depicted in FIG. 1. The cap 45 is comprised generally of a hollowed out cylinder 41 having disposed on the top thereof a ring member 43. The elastomeric member 20 extends over the top of the cylinder 41 and has an aperture therethrough so as to permit the interconnection of the ring 43 to the cylinder 41. In one embodiment, the elastomeric member 20 is connected to the plug 17 in the manner shown in FIG. 1. However, the opposed end of the elastomeric member 20 includes the cap 45 of FIG. 3. The purpose of the cap 45 is twofold. First, it facilitates the stretching of the elastomeric member so as to locate it about the plunger 14 as shown in FIG. 1. When the infuser 10 is being readied for use, the user will grasp the ring 43 thus extending the elastomeric member 20 and will thence dispose the cylinder 41 about the end of the plunger 14 so as to more securedly attach the elastomeric member 20 to the plunger 14. Yet an additional purpose of the cap 14 is to provide a means for supporting the infuser 10 on the user. More particularly, the ring member 43 is provided so as to facilitate pendantly disposing the infuser 10 by means of the ring 43 from the apparel of the user by means of a safety pin, clip, or the like.

Figure 4:
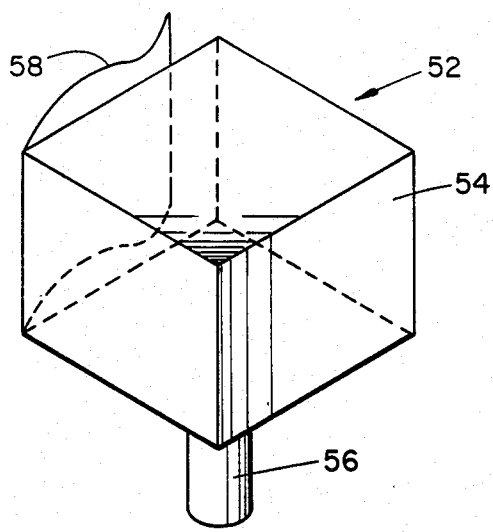
FIG. 4 is a pictorial view of an alarm element for use with the apparatus depicted in FIG. 1.

With reference to FIG. 4, a pictorial view is therein shown of an alarm element adapted for use with the apparatus depicted in FIG. 1. It is frequently desirable for the user of the infuser 10 of the present invention to perceive an audible alarm indicating when a predetermined amount of medicament is left in the infuser so that the user may take steps to have another dosage ready for use. Accordingly, it is an additional feature of this invention to provide for a means of audibly indicating when the plunger 14 and barrel 12 are in a preselected spatial positioning in the longitudinal direction relative to one another. In other words, it would be desirable to provide an audible indication of when the plunger 14 is disposed so far within the barrel 12 that very little of the medicament is left to be dispensed by the infuser 10.

The alarm element 52 depicted in FIG. 4 is intended to perform this function. Closer reference to FIG. 4 will indicate that a suitable means for attaching the alarm element 52 to the plunger 14, preferably at a location 50, may be provided by means of a convenient clip 58 or the like. It will be noted from FIG. 4 that the alarm element 52, in addition to being comprised of the clip 58, further includes a circuit housing 54 and switch member 56. When the alarm element 52 is clipped to the plunge 14 at location 50, when the plunger 14 moves longitudinally downwards into the barrel 12 sufficiently, the switch element 56 will contact the upper portion 19 of the barrel 12 so as to set off the audible alarm. Inasmuch as the alarm element 52 may be located anywhere along the plunger 14 merely by sliding the alarm element 52 along the plunger 14, adjustment can be made to provide an alarm at any preselected time preceding the exhaustion of the drug in the infuser 10. In some cases, it may accordingly be desirable to provide written indications on the plunger 14 indicating the appropriate placement in the longitudinal direction of the alarm element 52 thereon to achieve the alarm at the desired time.

When the plunger 14 has been thus moved by means of the elastomeric member 20 into the barrel 12 an appropriate distance, the switch element 56 will contact the upper portion 19 of the barrel 12, thus setting off the audible alarm.

Figure 5:
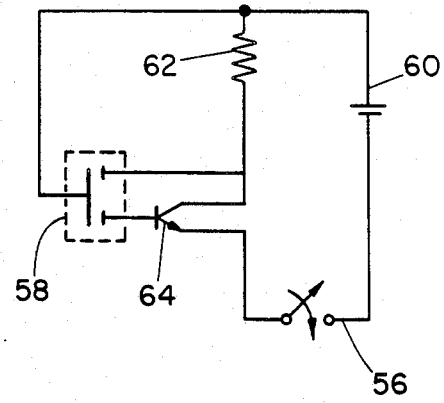
FIG. 5 is an alarm circuit portion of the alarm element of FIG. 4.

Reference to FIG. 5 indicates an illustrative general schematic circuit for performing the alarm function desired. This circuit will preferably be contained within the circuit housing 54 and will be comprised of a battery 16, the aforementioned normally open switch 56, a piezoelectric speaker element 58, an amplifying transistor 64, and biasing resistor 62. It will be appreciated that the switch 56 is preferably one which will close upon contact of the lowermost portion with the portion 19 of the barrel 12. Moreover, the switch 56 will be preferably one in which once this contact is made, the circuit housing 54 is permitted to continue moving with the plunger 14 in a downwards direction while maintaining the closure of the switch 56.

It is therefore apparent that the present invention is one well adapted to obtain all of the advantages and features hereinabove set forth, together with other advantages which will become obvious and apparent from a description of the apparatus itself. It will be understood that certain combinations and subcombinations are of utility and may be employed without reference to other features and subcombinations. Moreover, the foregoing disclosure and description of the invention is only illustrative and explanatory thereof, and the invention admits of various changes in the size, shape and material composition of its components, as well as in the details of the illustrated construction, without departing from the scope and spirit thereof.

What is claimed is:

1. An intravenous fluid infusion device for infusing a fluid into a patient at a controlled flow rate, comprising:
   a cylindrical houding unit;
   an outlet tubing in fluid communication with said housing unit;
   a syringe housing disposed partially within said housing unit;
   a syringe plunger disposed at least partially within said syringe housing;
   a control unit disposed within said housing unit and providing fluid communication between said syringe housing and said tubing; and
   an elastomeric member means extending radially outwards of said housing unit and said syringe housing and further extending from the proximal end of said housing unit to the distal end of said syringe plunger, said elastomeric member means being for providing a longitudinal force of preselected varying magnitude over time between said housing unit and said syringe plunger.

2. The apparatus of claim 1, wherein said control unit includes a flow control valve means for providing a preselected flow rate of said fluid from within said housing through said control unit to said tubing.

3. The apparatus of claim 2, wherein said syringe housing is in slidably releasable assembly with said housing unit.

4. The apparatus of claim 3, wherein
   said control unit includes a first connector means disposed at its distal end; and
   said syringe housing includes a second connector means disposable at its proximal end for releasable fluid-tight matingly sealing engagement with said first connector means.

5. The apparatus of claim 4, wherein said first and second connector means are threaded.

6. The apparatus of claim 5, wherein elasticity of said elastomeric member is preselected in functional relation to a desired preselected flow rate of said fluid through said tubing over time.

7. The apparatus of claim 6, wherein said preselected flow rate is constant.

8. The apparatus of claim 6, wherein said preselected flow rate is non-linear.

9. The apparatus of claim 5, wherein said control valve includes an orifice extending therethrough having a size preselected in functional relation to a desired preselected flow rate of said fluid through said tubing over time.

10. The apparatus of claim 9, wherein said housing unit, said control unit, said syringe housing, and said syringe plunger are all coaligned along a common longitudinal axis and wherein said elastomeric member comprises first and second elongate bands disposed in diametrically opposed facing relation on either side of said axis.

11. An infusion device comprising:
    syringe means defining a cavity for containing fluid and comprising a syringe housing and a syringe plunger in coaxial alignment alongitudinal axis and in slidable engagement;
    tube means in fluid connection with said cavity for delivering said fluid from said cavity through said tube means to a patient; and
    elongate elastomeric band means having a preselected coefficient of elasticity and interconnected between said syringe housing and said syringe plunger for decreasing the volume of said cavity at a preselected controlled rate varying over time as a function of said preselected coefficient of elasticity.

12. The apparatus of claim 11, wherein said band means comprises a plurality of rubber strips each disposed radially outwards of said syringe means and extending parallel to said axis and terminating at a proximal end of said syringe housing and at a distal end of said syringe plunger.

13. The apparatus of claim 12, wherein said plurality of rubber strips comprises first and second diametrically opposed strips.

14. The apparatus of claim 13, further including a control unit disposed between said syringe means and said tubing means for controlling the flow rate of said fluid through said tubing means.

15. The apparatus of claim 14, wherein
said control unit includes a control valve having an orifice extending therethrough; and wherein
the size of said orifice and the coefficient of elasticity of said band means are preselected in functional relation to a desired flow rate of said fluid through said tube means.

16. The apparatus of claim 15, wherein said control valve is removably disposed within said control unit.

17. A method of charging an infusion device with fluid having a housing unit, an outlet tube in fluid communication with said housing unit, a syringe housing slidably disposable partially within said housing unit, a syringe plunger slidably disposable within said syringe housing, an elastomeric member interconnected between said housing unit and said syringe plunger, a control unit contained within said housing unit and providing fluid communication between said outlet tube and a cavity defined by said syringe housing and said syringe plunger, a distal portion of said control unit and a proximal portion of said syringe housing being releasably interconnectable, and a filler needle, said method comprising:

attaching said filler needle to said proximal portion of said syringe housing;
introducing said filler needle into a reservoir of said fluid;
withdrawing said syringe plunger partially from said syringe housing to fill said cavity with said fluid;
removing said filler needle from said proximal end of said syringe housing;
inserting said syringe housing into said housing unit;
interconnecting said proximal end of said syringe housing to said distal end of said control unit; and
interconnecting said elastomeric member between said syringe plunger and said syringe housing.

18. The method of claim 17, further including:
providing a sealant on the inside surface defined by said housing unit or the outside surface defined by said syringe housing prior to said inserting of said syringe housing into said housing unit.

19. The method of claim 17, further including:
disposing a control valve having an orifice preselected in functional relation to a desired flow rate of said fluid through said tube within said control unit prior to said inserting of said syringe housing in said housing unit.

20. The method of claim 17, further including:
preselecting said elastomeric member prior to said interconnecting said elastomeric member to have a coefficient of elasticity preselected in functional relation to said preselected flow rate.

* * * * *